US00PP28231P3

(12) United States Plant Patent
Olesen

(10) Patent No.: US PP28,231 P3
(45) Date of Patent: Aug. 1, 2017

(54) COMPACT FLORIBUNDA ROSE PLANT NAMED 'POULCAS045'

(50) Latin Name: ***Rosa* hybrid**
Varietal Denomination: Poulcas045

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 12 days.

(21) Appl. No.: 14/756,276

(22) Filed: Aug. 20, 2015

(65) Prior Publication Data

US 2017/0055405 P1 Feb. 23, 2017

(51) Int. Cl.
*A01H 5/02* (2006.01)

(52) U.S. Cl.
USPC ..... Plt./151

(58) Field of Classification Search
USPC ..... Plt./151
See application file for complete search history.

(56) References Cited

PUBLICATIONS

Poulsen Roser A/S "National Parks-Perfection by Poulsen" Oct. 2012 (1 page).*

* cited by examiner

*Primary Examiner* — Susan McCormick Ewoldt

(57) ABSTRACT

A new garden rose plant of the compact floribunda class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas045'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2004 and the resulting seeds were planted in a controlled environment in Fredensborg, Denmark. The new variety, named 'Poulcas045', originated as a single seedling from the stated cross.

The new variety may be distinguished from its male pollen parent and female seed parent primarily by the following characteristics. The female seed parent has pink flowers while the new variety has red flowers. The male pollen parent has 5 to 7 flowers per flowering branch, while the new variety has 15 to 25 flowers per flowering branch.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas045' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulcas045' was selected in the spring of 2005 by the inventor as a single plant from the progeny of the aforementioned hybridization.

Asexual reproduction of 'Poulcas045' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulcas045' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas045'.

Specifically illustrated in FIG. 1 of the drawings are open flowers at various stages of development, flower petals detached, and the flower in parts.

Figure 1:
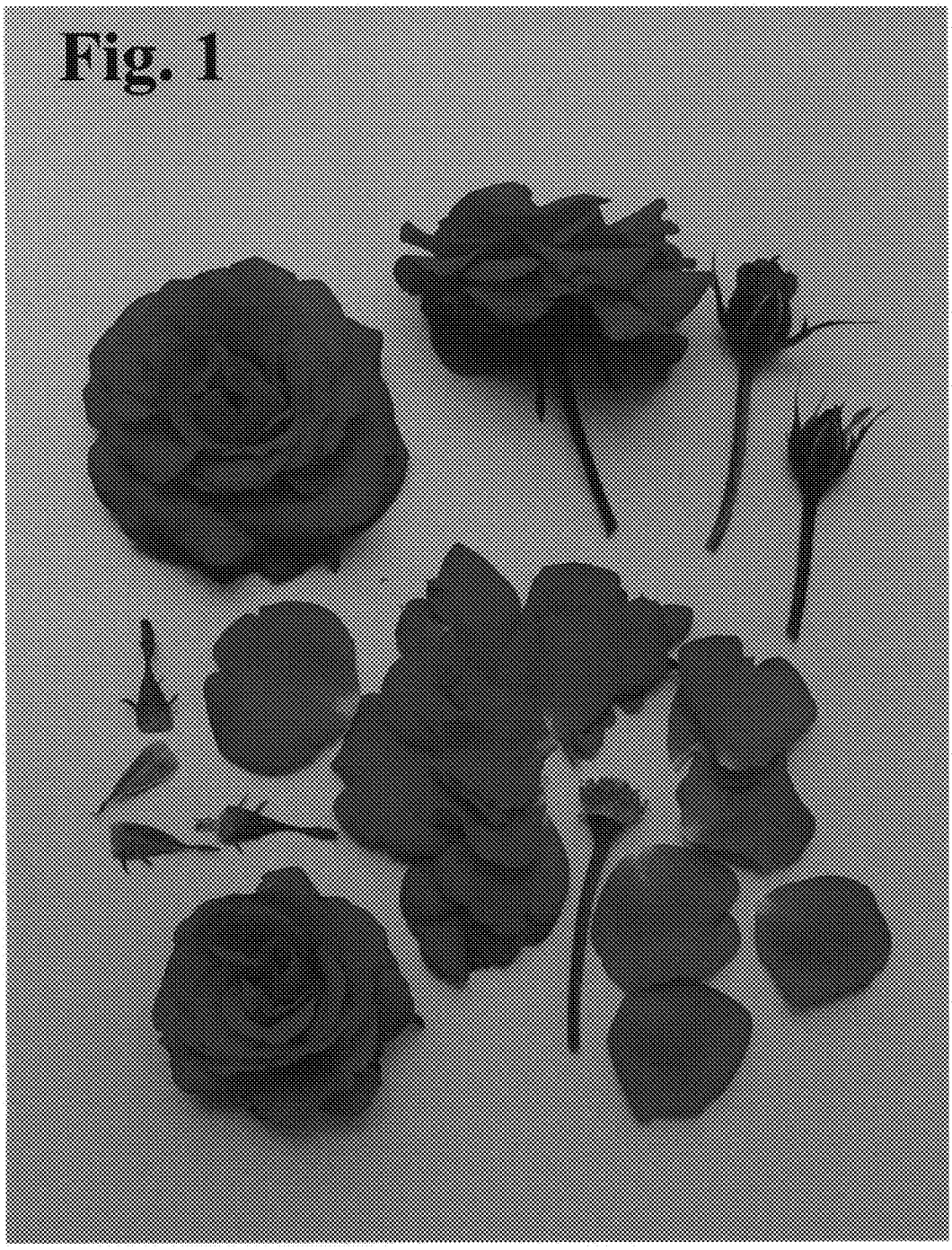
Figure 2:
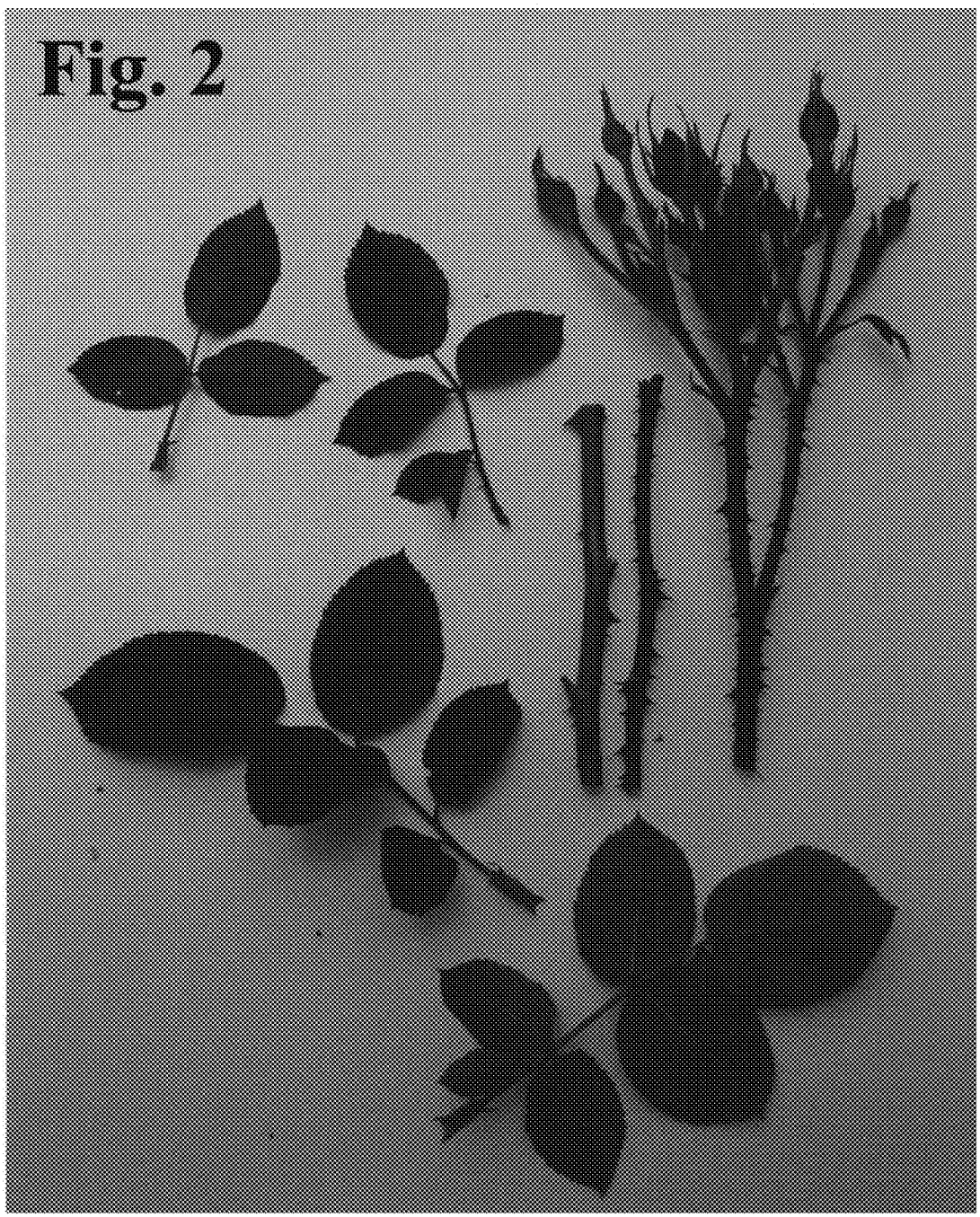

Specifically illustrated in FIG. 2 of the drawings are juvenile leaves showing anthocyanin, mature leaves, stems, and a flowering branch showing multiple flower buds. Plants shown are 2 years of age.

DETAILED DESCRIPTION OF THE VARIETY

The following is a description of 'Poulcas045', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poultry', U.S. Plant patent application Ser. No. 10/976,225, now abandoned, are compared to 'Poulcas045' in Chart 1.

CHART 1

| | 'Poulcas045' | 'Poultry' |
|---|---|---|
| Petal Count | 30 petals | 70 to 80 petals |
| Flower Diameter | 80 mm | 50 to 80 mm |
| General Tonality of Flower Color | Red Group 45B | Red Group 53A |

Flower and Flower Bud

Blooming habit: Continuous.

Flower bud:

*Size*.—Upon opening, 25 mm in length from base of receptacle to end of bud. Bud diameter is 12 mm.

*Bud form*.—Ovoid.

*Bud color*.—As sepals divide petals are Greyed-Purple Group 183A and Red Group 46B.

*Sepal inner surface*.—Color: Yellow-Green Group 145A with anthocyanin the color of Greyed-Purple Group 183C. Surface: Lightly pubescent.

*Sepal outer surface*.—Color: Yellow-Green Group 144A with strong anthocyanin Greyed-Purple Group 183A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—35 mm long, 10 mm wide.

*Receptacle*.—Texture: Smooth. Size: 5 mm in height, 6 mm wide. Color: Yellow-Green Group 144A with strong anthocyanin the color of Greyed-Purple Group 183A. Shape: Campanulate.

*Pedicel*.—Surface: Rough with many small prickles. Length: 40 to 50 mm. Diameter: 3 mm on average. Color: Yellow-Green Group 144A with strong anthocyanin the color of Greyed-Purple Group 183A. Strength: Strong.

*Peduncle*.—Length: 3 to 10 cm. Diameter: About 4 mm. Color: Yellow-Green Group 146A with strong anthocyanin the color of Greyed-Purple Group 183A. Texture: Rough with many small prickles.

Flower bud development: Flower buds are borne in panicles of 15 to 25 flower buds per stem. Panicles are about 20 cm in diameter.

Flower bloom:

*Fragrance*.—Moderate, old rose scent.

*Duration*.—The blooms have a duration on the plant of approximately 10 days. Petals fall cleanly away from plant after flowers have fully matured.

*Size*.—Flower diameter is 80 mm when open. Flower depth is 30 mm.

*Flower shape*.—Rosette, very double flower with many slightly overlapping petals of different sizes.

*Shape of flower, side view*.—The upper portion is a flattened convex. The lower portion is concave.

Petalage: Under normal conditions, flowers have 30 petals total, 5 to 7 of which are petaloids.

General tonality of flower: Open flowers are Red Group 45B.

Petal color:

*Upon opening, outer petals*.—Upper surface: Red Group 45B. Lower surface: Red Group 47B.

*Upon opening, inner petals*.—Upper surface: Red Group 45B. Lower surface: Red Group 47B.

*Basal petal spots, upon opening*.—Upper surface: Yellow Group 7A. Lower surface: Yellow Group 7A.

*After opening, outer petals*.—Upper surface: Red Group 45B. Lower surface: Red Group 47B.

*After opening, inner petals*.—Upper surface: Red Group 45B. Lower surface: Red Group 47B.

*Basal petal spots, after opening*.—Upper surface: Yellow Group 7A. Lower surface: Yellow Group 7A.

Petals:

*Petal reflex*.—Moderately reflexed.

*Margin*.—Entire. Moderate undulations.

*Shape*.—Generally broad elliptical. Apex shape: Rounded. Base shape: Rounded.

*Size*.—About 40 mm (l)×40 mm (w).

*Texture*.—Smooth.

*Thickness*.—Average.

Petaloids:

*Size*.—20 mm (l) by 20 mm (w).

*Quantity*.—5 to 7.

*Shape*.—Irregular.

*Color*.—Upper surface is Red Group 45B. Lower surface is Red Group 47B. Petaloid basal zone is colored Yellow Group 7A on the upper and lower surfaces.

Reproductive flower parts:

*Pollen*.—None observed.

*Anthers*.—Size: 2 mm in length. Color: Greyed-Yellow Group 162A. Quantity: 65 on average.

*Filaments*.—Color: Yellow Group 5A. Length: 5 mm.

*Pistils*.—Length: 6 mm. Quantity: 40 on average.

*Stigmas*.—Color: Orange-White Group 159A.

*Styles*.—Color: Greyed-Red Group 181D.

*Location of stigmas*.—Superior in location relative to the length of the filaments and the height of the anthers.

*Hips*.—None observed to date.

Plant

Plant growth: Upright, bushy. Plants are 60 cm in height, and 50 cm wide.

Stems:

*Color*.—Juvenile growth: Greyed-Purple Group 187A. Mature growth: Yellow-Green Group 144A.

*Length*.—On average, canes are 30 cm from the base of the plant to the flowering portion.

*Diameter*.—8 mm.

*Internodes*.—On mature canes about 40 mm between nodes.

*Surface texture*.—Young wood: Rough with small prickles. Older wood: Smooth.

Long prickles:

*Incidence*.—7 prickles per 10 cm of stem.

*Size*.—Average length of prickles on mature stems is 5 mm.

*Shape*.—Upper portion is linear. Lower portion is concave.

*Color*.—Juvenile prickles: Greyed-Purple Group 187A. Mature prickles: Greyed-Purple Group 187B.

Plant foliage:

*Compound leaf*.—About 160 mm (l)×100 (w).

*Quantity*.—2 leaves per 10 cm of stem on average.

*Leaf bearing angle to the stem*.—45 degrees.

*Color of juvenile foliage*.—Upper side: Yellow-Green Group 146A with strong intonations of Greyed-Purple Group 187A. Lower side: Greyed-Purple Group 187A.

*Color of mature foliage*.—Upper side: Yellow-Green Group 147A. Lower side: Yellow-Green Group 147B.

Plant leaves and leaflets:

*Stipules*.—Size: 25 mm long, 6 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 1.5 mm.

*Upper surface*.—Color: Yellow-Green Group 144A with light intonations of Greyed-Red Group 179A.

*Lower surface*.—Color: Yellow-Green Group 144A.

*Rachis*.—Length: 65 mm. Upper surface: Color: Yellow-Green Group 144A with light intonations of Greyed-Red Group 179A.

*Lower surface*.—Color: Yellow-Green Group 144A. Observations: Small prickles

*Leaflet*.—Quantity: Normally 5 to 7 leaflets. Margins: Serrated. Size: On average terminal leaflets are 55 mm long, 50 mm wide. Shape: Generally ovate. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the compact floribunda rose class named 'Poulcas045', substantially as illustrated and described herein, due to its abundant red flowers, disease resistance, and extended period of bloom.

* * * * *